United States Patent [19]

Frazer

[11] Patent Number: Plant 6,873

[45] Date of Patent: Jun. 20, 1989

[54] DIEFFENBACHIA HYBRIDA ALOHA

[75] Inventor: Edwin J. Frazer, Brisbane, Australia

[73] Assignee: Hoffman Plant Laboratories, Inc., Santa Paula, Calif.

[21] Appl. No.: 23,610

[22] Filed: Mar. 9, 1987

[51] Int. Cl.[4] ..... A01H 5/00

[52] U.S. Cl. ..... Plt./88

[58] Field of Search ..... Plt./88

*Primary Examiner*—Robert E. Bagwill

[57] ABSTRACT

A new and distinct cultivar of Dieffenbachia known as Dieffenbachia Hybrida Aloha, which is a seedling cross between Wilsonii and Perfection.

1 Drawing Sheet

The invention comprises a new and distinct cultivar of Dieffenbachia known as Dieffenbachia Hybrida Aloha.

The new cultivar is a product of a seedling cross between Wilsonii and Perfection.

The following observations, measurements and values describe plants grown in Alva, Fla. under greenhouse conditions that closely approximate those generally used in horticultural practice. All color references are measured against The Royal Horticultural Society Colour Chart. Colors are approximate as color depends on horticultural practices such as light level and fertilization rate among others.

The following traits have been repeatedly observed to be characteristics which in combination distinguish Dieffenbachia Aloha from other commercially available Dieffenbachia.

DISTINCTIONS

1. Compacta type with minor breaks in the pattern.
2. The leaves are larger than Compacta and come to a point much more rapidly than Compacta.
3. Has slightly fewer breaks than Compacta.
4. Leaves are forced sideways by the quantity of leaves on the plant.
5. The main stem is short for a Dieffenbachia with leaves this large.
6. The breaks grow almost as tall as the main shoot.
7. The midribs is flexible enough to permit bending the leaf without damage.

The appearance and distinctive character of Aloha is shown in the FIGURE which is a true color photograph of the cultivar in an eight-inch pot.

DESCRIPTION

Propagation: Asexual production either through tissue culture or division.

Plant: In a 6 inch pot, Aloha will be approximately 16 cm to 20 cm from the soil surface to the junction of the petioles of the last two unrolled leaves and approximately 50 cm to 60 cm in width after approximately 26 weeks to 36 weeks under appropriate growing conditions from tissue culture. All measurements are based on the above parameters.

Stem:

*Growth pattern.*—The stem is erect in growth and will be approximately 1.5 cm to 1.9 cm in diameter 5 cm above the soil surface. Internode distance will be approximately 1.5 cm to 1.7 cm at a height of 3 cm above the soil.

*Color.*—The stem is light green.

Petiole (based on the third expanded leaf from apex of the main shoot):

*Pattern.*—The petiole has fleshy edges extending from the midrib that will be referred to as wings. The wings will be approximately 5 mm to 7 mm wide 1 cm below the leaf base. The wings extend from the base of the petiole to within approximately 0.8 cm to 1.1 cm of the leaf base. The apex of the wings is emarginate. The petiole follows the stem axis but diverges from the axis approximately 3.5 cm to 3.9 cm from the leaf base forming a horizontal distance from the edge of the stem to the leaf base of approximately 1.3 to 1.7 cm.

*Physical dimensions.*—The petiole will be approximately 11.0 cm to 11.5 cm from its base to the base of the leaf. The petiole will be approximately 6 cm to 8 cm in diameter one-half way between the top of the wing to the bottom of the leaf.

*Color and color pattern.*—The petiole wings will be green and the midrib will be light green.

Leaf:

*Growth pattern.*—The leaf will be ovate with a aristate/cuspidate apex and a cordate base. The margin is entire. The leaf is asymmetric with the side of the leaf unrolling first having less surface area and less undulations on the leaf margin than the side unrolling last. The leaf is oriented 10° to the stem axis at the time of full unrolling changing to 50° to the stem axis as more leaves unroll above it. The midrib droops slightly over the length of the leaf. The leaf blade is flat from the midrib to the margin.

*Physical dimensions.*—For the potsize and growing time indicated, the largest leaf will be approximately 26 cm to 30 cm long and approximately 12 cm to 14 cm wide. An average sized leaf will be approximately 16 to 20 cm long and approximately 9 to 11 cm wide. The leaf thickness is thick.

*Midrib.*—The midrib is thick and white with numerous green blotches increasing toward the base.

*Primary veins.*—The primary veins are sunken into the adaxial side and protruding out of the abaxial side.

*Color and pattern.*—The adaxial surface of the mature, older leaf has a midrib color of 137C, and a leaf blade background color of 139A, with small blotches of 157C. The abaxial surface of the mature, older leaf has a midrib color of 145D on the basal-surface, and on the sides of the midrib a color that is darker than 138B; the leaf blade background color is darker than 138B, blotched with small areas of 149D. The adaxial surface of the newly-opened leaf has amidrib color of 157, blotched with 144A, and a leaf blade color of 139A, blotched with areas of 157C and 150D. The abaxial surface of the newly-opened leaf has a midrib color of 145A on the basal surface and 191A on the sides, and a leaf blade background color of 191A, blotched with 157C.

*Texture.*—The leaves are thick and lightly ribbed.

Axillary breaks: There will be approximately 13 to 17 axillary breaks with at least 1 leaf expanded. Leaves will show color by the second leaf and will have true color and pattern by the fourth leaf.

Inflorescences: Not present.

Roots: Thick white roots with finer laterals.

General observations: Dieffenbachia Aloha is a Compacta type about the same height and width as Compacta but differs in the following ways. Aloha has larger leaves that remain broader further out on the midrib than Compacta. Aloha has small breaks in the color pattern. Aloha has slightly fewer breaks than Compacta but is just as full due to the larger leaf and the breaks that form major shoots almost as tall as the main shoot.

The midrib is flexible enough so that the leaf can be bent without damage.

I claim:

1. A new and distinct cultivar of Dieffenbachia as described and illustrated.

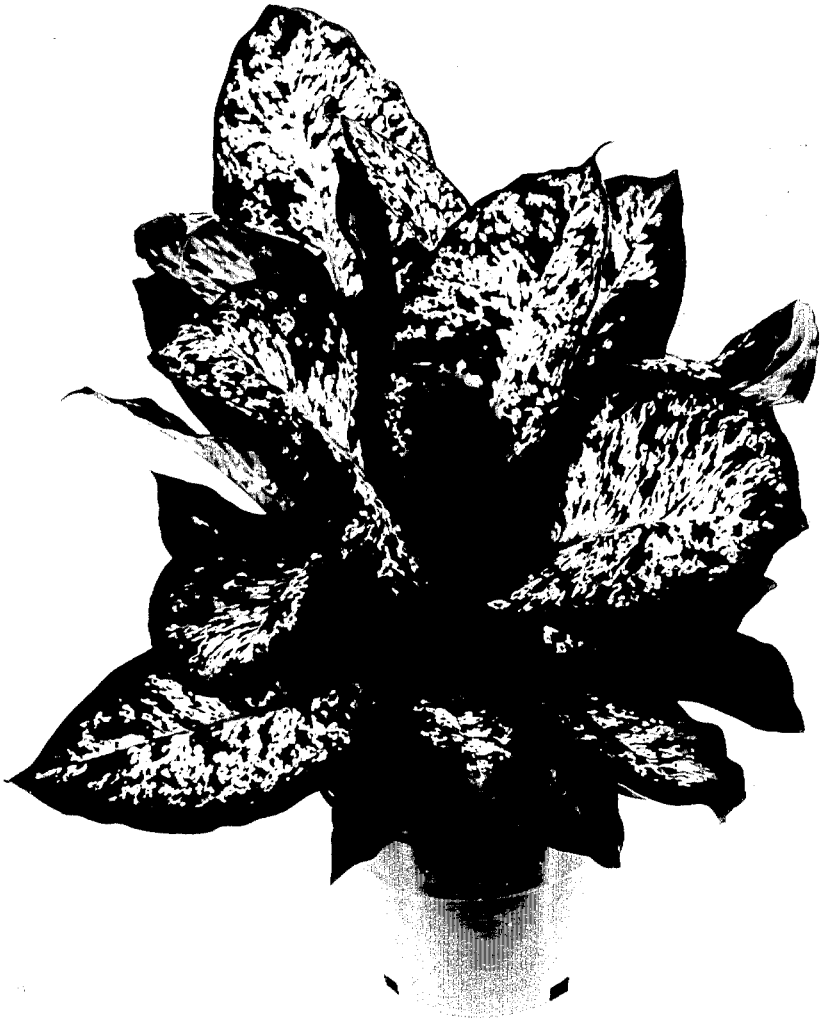

* * * * *